United States Patent
Wu

(10) Patent No.: US 9,410,182 B2
(45) Date of Patent: Aug. 9, 2016

(54) PHOSPHATASE COUPLED GLYCOSYLTRANSFERASE ASSAY

(75) Inventor: Zhengliang L. Wu, Edina, MN (US)

(73) Assignee: Bio-Techne Corporation, Minneapolis, MN (US)

( * ) Notice: Subject to any disclaimer, the term of this patent is extended or adjusted under 35 U.S.C. 154(b) by 0 days.

(21) Appl. No.: 13/699,175

(22) PCT Filed: May 24, 2010

(86) PCT No.: PCT/US2010/035938
§ 371 (c)(1),
(2), (4) Date: Nov. 20, 2012

(87) PCT Pub. No.: WO2011/149448
PCT Pub. Date: Dec. 1, 2011

(65) Prior Publication Data
US 2013/0065262 A1  Mar. 14, 2013

(51) Int. Cl.
  *C12Q 1/48* (2006.01)
  *C12Q 1/42* (2006.01)
(52) U.S. Cl.
  CPC .. *C12Q 1/42* (2013.01); *C12Q 1/48* (2013.01); *G01N 2333/914* (2013.01); *G01N 2333/91091* (2013.01)
(58) Field of Classification Search
  CPC ............ C12Q 1/48; C12Q 1/42; C12N 9/108; C12N 9/14; C12Y 306/01005; G01N 2333/91091; G01N 2333/914
  USPC ...................... 435/15, 18, 193, 195
  See application file for complete search history.

(56) References Cited

U.S. PATENT DOCUMENTS

| | | | |
|---|---|---|---|
| 6,551,790 B2* | 4/2003 | Trubetskoy et al. | 435/15 |
| 7,247,300 B1* | 7/2007 | Chen et al. | 424/94.6 |
| 7,521,250 B2 | 4/2009 | Hamachi | |
| 2008/0233592 A1 | 9/2008 | Lowery | |

FOREIGN PATENT DOCUMENTS

| | | | |
|---|---|---|---|
| WO | 9410340 A1 | | 5/1994 |
| WO | WO 00/42214 | * | 7/2000 |
| WO | 02092845 A2 | | 11/2002 |
| WO | WO 2008/036139 A2 | * | 3/2008 |

OTHER PUBLICATIONS

Wu et al., R&D Systems Poster, "Universal Phosphatase-Coupled Glycosyltransferase Assay", Apr. 2010, 3 pages.*
"Malachite Green Phosphate Detection Kit", Research and Diagnostic Systems, Inc. Catalog No. DY996, Feb. 4, 2010, 6 pages.*
Zhu et al., Analytica Chimica Acta 636:105-110, 2009.*
Motomizu et al., Analytica Chimica Acta 211:119-127, 1988.*
Schachter et al., Methods Enzymol. 98:98-134, 1983.*
Unverzagt et al., J. Am. Chem. Soc. 112:9308-9309, 1990.*
IUBMB Enzyme Nomenclature for EC 3.1.3.1, obtained from www.chem.qmul.ac.uk/iubmb/enzyme/EC3/1/3/5.html, last viewed on Apr. 13, 2015, 1 page.*
IUBMB Enzyme Nomenclature for EC 3.1.3.5, obtained from www.chem.qmul.ac.uk/iubmb/enzyme/EC3/1/3/5.html, last viewed on Apr. 13, 2015, 1 page.*
Compain et al., Bio. Med. Chem. 9:3077-3092, 2001.*
Lee et al., J. Biol. Chem. 277:49341-49351, 2002.*
Donovan R S et al., "A solid-phase glycosyltransferase assay for high-throughput screening in drug discovery research," Glycoconjugate Journal, vol. 16, No. 10, (Oct. 1, 1999), pp. 607-615.
Manu R M De Groeve et al., "Enzymatic production of α-d-galactose 1-phosphate by lactose phosphorolysis," Biotechnology Letters, vol. 31, No. 12, (Jul. 24, 2009), pp. 1873-1877.
Rowlands M G et al., "High-throughput screening assay for inhibitors of heat-shock protein 90 ATPase activity," Analytical Biochemistry, vol. 327, No. 2, (Apr. 15, 2004), pp. 176-183.
PCT International Search Report dated Sep. 30, 2010 for PCT/US2010/035938, from which the instant application is based, 3 pgs.
Written Opinion dated Sep. 30, 2010 for PCT/US2010/035938, from which the instant application is based, 5 pgs.
Wongkongkatep J et al., "Label-free, real-time glycosyltransferase assay based on a fluorescent artificial chemosensor," Angewandte Chemie, vol. 45, No. 4 (Jan. 16, 2006), pp. 665-668.

* cited by examiner

*Primary Examiner* — David J Steadman
(74) *Attorney, Agent, or Firm* — Fredrikson & Byron, P.A.

(57) ABSTRACT

A kit for detecting or measuring glycosyltransferase activity including a first reagent comprising a phosphatase and a second reagent comprising a free phosphate detector, and method of detecting and measuring glycosyltransferase activity. A sugar donor, an acceptor substrate, a glycosyltransferase enzyme and a phosphatase are combined and the amount of free phosphate present in the product is measured and used to calculate the activity of the glycosyltransferase enzyme.

5 Claims, 4 Drawing Sheets

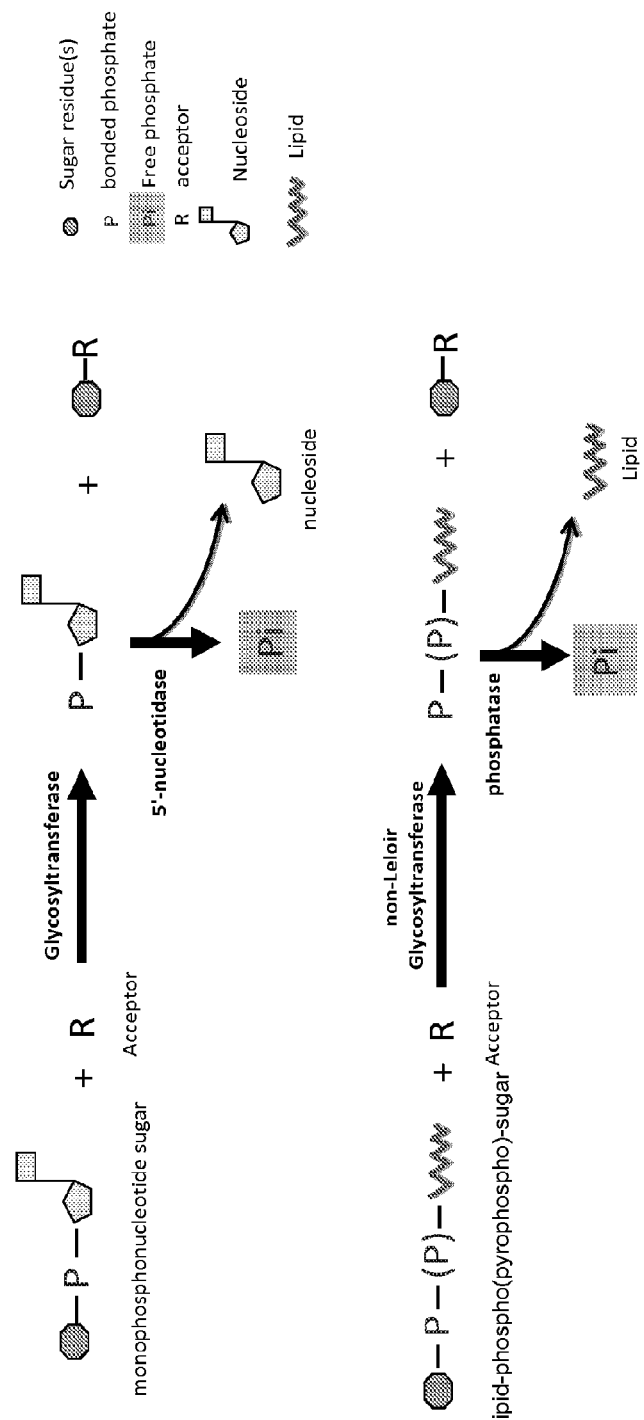
Figure 1
Figure 2
Figure 3

PHOSPHATASE COUPLED GLYCOSYLTRANSFERASE ASSAY

RELATED APPLICATIONS

This application is a 35 U.S.C. 371 national stage filing from, and claims priority to, International Application No. PCTUS2010/035938 filed May 24, 2010, the teachings of which are incorporated herein by reference.

BACKGROUND

Polysaccharides are extremely abundant and diverse, including structures such as cellulose, chitin, starch, and glycogen, to name just a few examples. Glycosylation is important not only to the formation of carbohydrates, but also glycoproteins, and glycolipids, cellular processes including protein folding, trafficking, recognition, and stability, cell growth, migration, communication, and immune response. It also plays a role in the virulence of many microorganisms.

The formation of carbohydrate molecules in biological systems depends upon glycosyltransferase enzymes, which perform the key function of transferring a monosaccharide or an oligosaccharide from a donor molecule to an acceptor. Given the abundance and structural diversity of carbohydrates, it is not surprising that there are numerous glycosyltransferase enzymes, each of which are specific to particular donor molecules and acceptor molecules. For example, it is estimated that the human genome encodes more than 200 glycosyltransferase genes.

Glycosyltransferase enzymes add sugar groups not only to polysaccharides but also to proteins and lipids to form, glycoproteins, and glycolipids. Most glycosyltransferases use activated nucleotide sugars as donor molecules. These glycosyltransferases are referred to as Leloir enzymes. A Leloir glycosyltransferase transfers the sugar group from a sugar nucleotide to a substrate molecule (e.g., sugar, protein or lipid), generating a nucleotide leaving group. The other glycosyltransferases, referred to as non-Leloir enzymes, use other donors such as lipid phosphosugars, resulting in leaving groups such as lipid phosphates.

Because of their key roles in development, cellular functions, and pathogenicity, it is desirable to monitor glycosyltransferase activity. For example, glycosyltransferases may be ideal targets for drug therapies, to promote, inhibit, or block their activities. A method of monitoring glycosyltransferase activity would therefore be very useful in the development of such drugs, among other uses.

Several methods have attempted to measure glycosyltransferase activity, but each of these methods suffers from certain difficulties which limit their usefulness. For example, one traditional method of assaying glycosyltransferases uses radioisotopes. However, besides involving the use of radioactivity, this method requires the use of a specific labeled compound and separation of the donor from the acceptor, which is a time consuming process. Thin-layer chromatography (TLC), high pressure liquid chromatography (HPLC) and LC-MS can also be used. However, these methods are limited by the lack of speed, expensive reagents and equipment and the high level of expertise which is required to perform them. Antibody labeling and fluorogenic compounds can also be used, with the antibodies and fluorogenic compounds specifically targeted to the nucleotide products. While these methods do not require separation of the donor and acceptor, the specific antibodies and fluorogenic compounds can be difficult to produce, resulting in high cost, and can entail long assay times and high background readings, making the results less sensitive than desired.

SUMMARY

Embodiments of the invention include assays and method of detecting and quantifying glycosyltransferase activity. In one embodiment, a kit for the detection of glycosyltransferase activity includes a first reagent comprising a phosphatase and a second reagent comprising a free phosphate detector. The phosphatase may be an apyrase such as ectonucleoside triphosphate diphosphohydrolase such as CD39L3 or a 5'-nucleotidase such as CD73. In some embodiments, the phosphatase may be an alkaline phosphatase. The kit may further include a phosphate free buffer. The kit may also include a phosphate standard, such as $KH_2PO_4$.

In some embodiments, the kit for detecting glycosyltransferase activity may include one or more nucleotides, such as UDP, GDP or CMP. The kit may include a sugar donor, such as a sugar nucleotide. The kit may also include a sugar acceptor substrate. In some embodiments, the kit may include a glycosyltransferase enzyme.

Embodiments of the invention also include methods of assaying the activity of a glycosyltransferase enzyme. The method may include combining a sugar donor, an acceptor substrate, the glycosyltransferase enzyme and a phosphatase in a buffer solution to produce a product, and measuring the amount of free phosphate present in the product. The amount of free phosphate present in the sample may then be used to calculate the activity of the glycosyltransferase enzyme.

In some embodiments, the sugar donor, acceptor substrate and glycosyltransferase may be combined first, and then the phosphatase may be added. Alternatively, the sugar donor, acceptor substrate, glycosyltransferase and phosphatase may be combined at the same time in a coupling reaction.

In some embodiments, the sugar donor is a sugar nucleotide. In some embodiments, the sugar nucleotide is sugar diphosphonucleotide and the phosphatase is an apyrase, such as an ectonucleoside triphosphate disphosphohydrolase. In some embodiments, the sugar nucleotide is a sugar monophosphonucleotide and the phosphatase is a monophosphonucleotidase, such as a 5'-nucleotidase. In other embodiments, the sugar donor is a lipid phospho-sugar and the phosphatase is an alkaline phosphatase.

In some embodiments, the amount of free phosphate present in the sample may be measured by applying a colorimetric assay to the sample. In some embodiments, the application of the colorimetric assay includes combining the product with a first reagent comprising ammonium molybdate and sulfuric acid, then combining this with a second reagent comprising malachite green oxalate and polyvinyl alcohol, and then measuring the light absorbance of the product of step b at 620 nm. The amount of free phosphate may then be calculated from the measured light absorbance.

In other embodiments, the invention includes a method of determining whether a test substance affects the activity of a glycosyltransferase enzyme. The method may include combining a sugar donor, an acceptor substrate, the glycosyltransferase enzyme, a phosphatase, and a test substance in a buffer solution to produce a product, measuring the amount of free phosphate present in the product, using the measured amount of free phosphate to calculate the activity of the glycosyltransferase enzyme in the presence of the test substance, and comparing the activity of the glycosyltransferase enzyme in the presence of the test substance to a known or measured activity of the glycosyltransferase enzyme without the test substance.

The method may be used for screening a test substance for activity as an inhibitor of the glycosyltransferase. For example, the method may be used for screening a test substance for activity as an antimicrobial agent.

BRIEF DESCRIPTION OF THE FIGURES

FIG. 1 is a diagramatic representation of an exemplary reaction according to embodiments of the invention;

FIG. 2 is a diagramatic representation of another exemplary reaction according to embodiments of the invention;

FIG. 3 is a diagrammatic representation of another exemplary reaction according to embodiments of the invention;

DESCRIPTION

Figure 4:
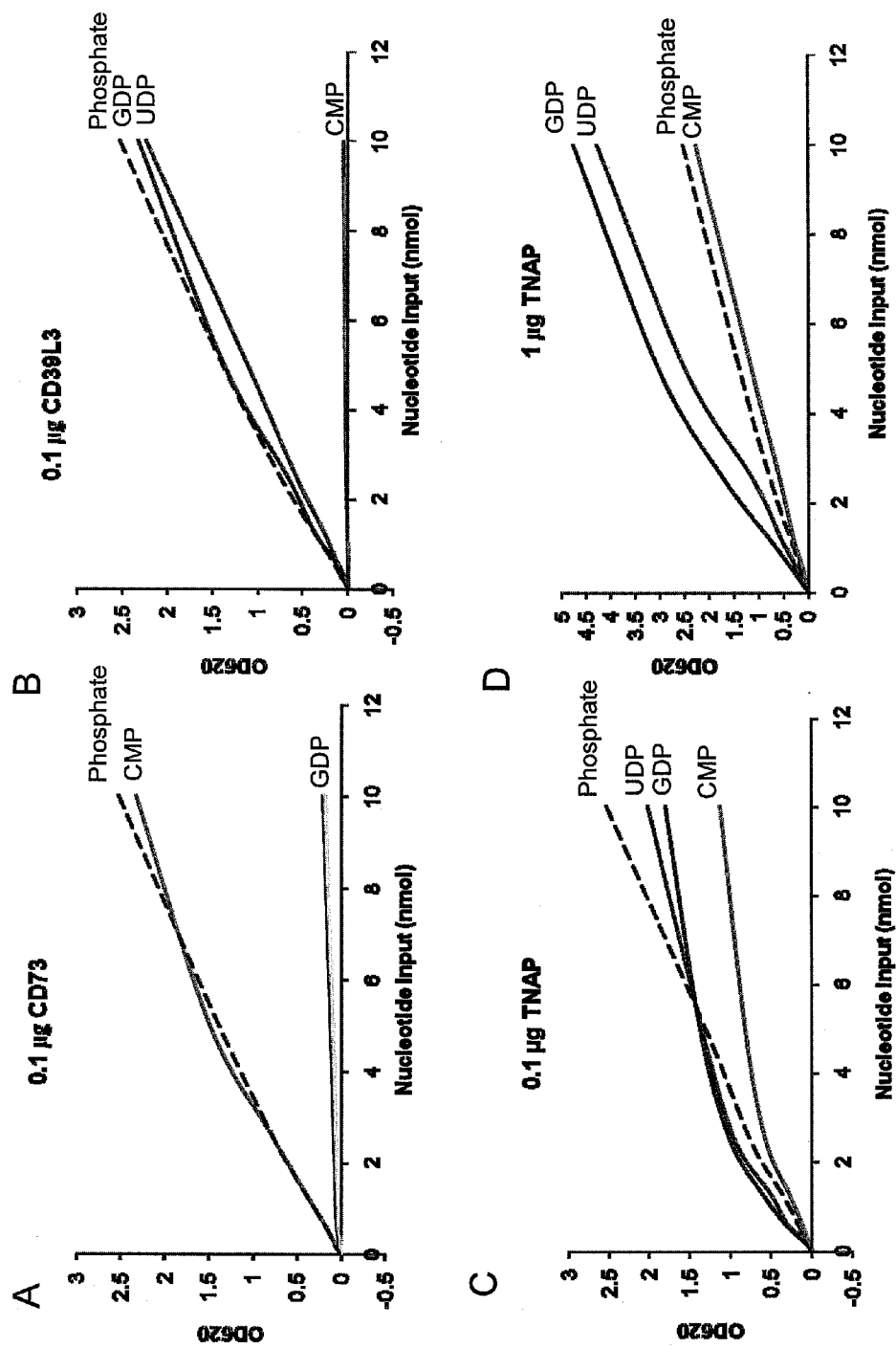
FIG. 4A is a graph of absorbance due to phosphate release from CMP by CD73.
FIG. 4B is a graph of absorbance due to phosphate release from GDP and UDP by CD39L3.
FIG. 4C is a graph of absorbance due to phosphate release from UDP, GDP and CMP by TNAP.
FIG. 4D is a graph of absorbance due to phosphate release by GDP, UDP, and CMP by TNAP.

Glycosyltransferase enzymes transfer a monosaccharide or oligosaccharide from a donor to an acceptor, resulting in a leaving group with the sugar removed and a glycosylated acceptor. Most glycosyltransferases are Leloir enzymes which use activated nucleotide sugars as donors. The remaining glycosyltransferase enzymes are non-Leloir enzymes which use other donors such as lipid-phosphosugars or lipid-pyrophosphosugars.

However, in all cases, the glycosylation reaction results in the sugar moiety transferring from the donor to the acceptor, producing a leaving group.

Nearly all sugar donors, for both Leloir and non-Leloir enzymes, include one or more phosphates between the sugar moieties and the nucleoside or lipid moieties. As a result, with the exception of sugar-1-phosphates, the phosphates present in the donors are not available to phosphatases prior to transfer of the monosaccharide. When a phosphatase is combined with a donor, no free phosphate is produced. In contrast, after the glycosyltransferase transfers the sugar from the donor to the acceptor, the phosphate of the donor, which had previously been blocked by the sugar, becomes exposed in the resulting leaving group. The removal of the sugar from the donor therefore makes the phosphate of the leaving group available for cleavage by a phosphatase. Embodiments of the invention employ one or more phosphatase enzymes to cleave the phosphate from the leaving group after transfer of the sugar, and then detect and/or measure the free inorganic phosphate produced. In other embodiments, the donor is a sugar-1-phosphate, which produces a free phosphate leaving group that can be detected and/or measured without the use of a phosphatase.

The amount of free phosphate produced and detected provides a quantitative measurement of the activity of the glycosyltransferase enzyme. For each sugar transfer performed by the glycosyltransferase, the phosphate of the donor substrate becomes available to the phosphatase. Depending upon the choice of phosphatase and number of cleavable phosphates present in the donor, the phosphatase may release either one or two phosphates from each leaving group. The amount of phosphate released can then be detected and measured, thereby providing a measurement of the glycosyltransferase activity.

Embodiments of the invention therefore provide methods of measuring the kinetics of glycosyltransferase reactions using non-radioactive methods. Furthermore, because the reactions can be performed in a multi-well plate and read with a multi-well plate reader, the methods may be used for high throughput screening.

Embodiments of the invention may be better understood by reference to examples of glycosylation reactions and free phosphate release as shown in FIGS. 1-3. In FIG. 1, a diphosphonucleotide sugar, such as UDP-sugar or GDP-sugar, serves as a donor. It is combined with an acceptor represented as R, and a glycosyltransferase enzyme, which catalyzes the transfer of the sugar from the donor to the acceptor. The result is a diphosphonucleotide leaving group having an exposed phosphate and a product, which is the acceptor with the transferred sugar group. A phosphatase, which in this example is an apyrase such as CD39L3, cleaves a single phosphate from the diphosphonucleotide, resulting in a free inorganic phosphate and a monophosphonucleotide. The free inorganic phosphate can then be detected, such as by a colorimetric assay. As can be seen, the amount of free phosphate produced directly correlates with the progress of the glycosyltransferase reaction.

In FIG. 2, the donor is a monophosphonucleotide sugar such as CMP-sialic acid. As in FIG. 1, the donor is combined with an acceptor, R, and a glycosyltransferase catalyzes the transfer of the sugar from the donor to the acceptor, resulting in a monophosphonucleotide leaving group having an exposed phosphate and a product which includes the sugar. A 5'-nucleotidase such as CD73 releases the phosphate from the monophosphonucleotide leaving group, resulting in a free inorganic phosphate and a nucleoside. The free inorganic phosphate can be detected as described herein, and the amount of phosphate again provides a measure of glycosyltransferase activity.

FIG. 3 depicts a non-Leloir reaction. The donor in this example is a lipid-phosphosugar or pyrophosphosugar. The acceptor substrate is depicted as R. The non-Leloir glycosyltransferase transfers the sugar from the donor to the acceptor, producing a leaving group which has an exposed phosphate. The phosphate is released from the leaving group by a lipid phosphate specific phosphatase or non-specific phosphatases such as tissue nonspecific alkaline phosphatase (TNAP), resulting in free inorganic phosphate and lipid.

The free inorganic phosphate may then be detected and/or measured to calculate the activity on the glycosyltransferase.

Embodiments of the invention rely on the selective removal of phosphate from donor molecules which have undergone transfer of the sugar, followed by detection of the free phosphate. Examples of phosphatases which may be used in embodiments of the invention include but are not limited to ectonucleoside triphosphate diphosphohydrolases, calcium activated nucleotidase 1, diphosphonucleotidases, 5'-nucleotidases, apyrases, alkaline phosphatases, and acid phosphatase. The specific phosphatase to be used may be selected based upon the identity of the donor, and the donor may be selected based upon the identity of the glycosyltransferase being assayed. For example, a diphonophonucleotidase or apyrases may be used when the donor is a diphosphonucleotide sugar in order to remove the $\beta$ phosphate from the diphosphonucleotide leaving group. A 5'-nucleotidase may be used when the donor is a monophosphonucleotide sugar in order to remove the α phosphate from the monophosphonucleotide leaving group. The phosphatases may be isolated from naturally occurring sources or may be produced recombinantly and many are commercially available. The phosphatases useful in embodiments of the invention also include any homologue proteins from different organisms and any mutational variations of any of the phosphatases described herein.

Examples of diphosphonucleotidases or apyrases which may be used in embodiments of the invention include, but are not limited to, members of the ectonucleoside triphosphate diphosphohydrolase (ENTPD) family including CD39L3 (ENTPD3), CD39 (ENTPD1), CD39L1 (ENTPD2), CD39L3 (ENTPD3), ENTPD4, CD39L4 (ENTPD5), ENTPD6, ENTPD7, and ENTPD8. Other diphosphonucleotidases which may be used in embodiments of the invention including a diphosphonucleotide sugar donor include calcium activated nucleotidase 1 (CANT1) and less specific alkaline and acid phosphatases, such as intestinal alkaline phosphatase (ALPI), tissue-nonspecific alkaline phosphatase (ALPL, also known at TNAP) and placental type alkaline phosphatase (PLAP), for example. In some embodiments, the phosphatase may be an apyrase, such as an apyrase from *S. tuberosum, Anopheles stephensi, Aedes albopictus, Aedes aegypti, Triatoma infestans, Escherichia coli, Caenorhabditis elegan*, or any yeast and mammalian species. In still other embodiments, the phosphatase may be commercial shrimp alkaline phosphatase (SAP), calf intestinal alkaline phosphatase (CIP) and potato alkaline phosphatase.

Examples of 5'-nucleotidases which may be used in embodiments of the invention include CD73, NT5DC1, NT5DC2, NT5DC3, cytosolic 5'-nucleotidase IA (NT5C1A), cytosolic 5'-nucleotidase IB (NT5C1B), cytosolic 5'-nucleotidase II (NT5C2), cytosolic 5'-nucleotidase III (NT5C3), NT5C3L, NT5DC4, and TNAP. Other phosphatases that may be used in reactions using a monophosphonucleotide sugar donor include any of the less specific alkaline phosphatases, such as intestinal alkaline phosphatase (ALPI), tissue-nonspecific alkaline phosphatase, and placental type alkaline phosphatase (PLAP).

Alternatively, the phosphatase may be the commercial shrimp alkaline phosphatase (SAP), calf intestinal alkaline phosphatase (CIP) or potato alkaline phosphatase.

Non-Leloir glycosyltranferases can also be assayed. The phosphates may be released from the leaving groups of such reactions using undecaprenyl-diphosphatase, dolichyl pyrophosphatase, or tissue non-specific alkaline phosphatase such as TNAP or other alkaline phosphatases such as intestinal alkaline phosphatase (ALPI), placental type alkaline phosphatase (PLAP), shrimp alkaline phosphatase (SAP), calf intestinal alkaline phosphatase (CIP) and potato alkaline phosphatase, for example.

Glycosyltransferase enzymes are specific to particular sugar donors and acceptors.

Because of the selectivity of glycosyltransferase enzymes, the choice of donor and acceptor used in embodiments of the invention will depend upon the specific glycosyltransferase enzyme which is being assayed. Glycosyltransferases generally have activity only with very specific donor substrates. In contrast, some glycosyltransferases may have activity with many different acceptors, while others may have activity with only one acceptor. Any glycosyltransferase which transfers a sugar from a donor, resulting in the donor having an exposed phosphate, may be used in embodiments of the invention. Examples of glycosyltransferases which may be used in embodiments of the invention include, but are not limited to, glucosyltransferases such as toxin *Clostridium difficile* B (TcdB), fucosyltransferases such as fucosyltransferase 7 (Fut7), sialyltransferases such as beta-galactoside alpha-2,6-sialyltransferase 1 (ST6Gal 1), galactosyltransferases, N-acetylgalactosaminyltransferases, and N-Acetylglucosaminyltransferases, mannosyltransferases and glucuronyltransferases. Glycosyltransferases may be obtained from recombinant sources or may be purchased from commercially available sources. The sugar donor used in embodiments of the invention may be any donor such as a monosaccharide or oligosaccharide donor which, after removal of the sugar by a glycosyltransferase, results in a leaving group containing one or more phosphate residues that can be released by a phosphatase. For example, donors which may be used in embodiments of the invention include diphosphonucleotide sugars, monophosphonucleotide sugars, lipidphosphosugars, and lipid-pyrophosphosugars. Alternatively, sugar-1-phosphates may be used as sugar donors and are preferably used without a coupling phosphatase, because a phosphate is the leaving group in these reactions. Examples of diphosphonucleotide sugars which may be used in embodiments of the invention include uridine diphosphate glucose (UDP-glucose), UDP-galactose, UDP-N-acetylglucosamine (UDP-GlcNAc), UDP-xylose, UDP-glucuronic acid, guanosine diphosphate mannose (GDP-mannose), GDP-fructose, UDP-N-acetylgalactosamine (UDP-GalNAc), GDP-fucose, dTDP-rhamnose, UDP-galacturonic acid, CMP-3-deoxy-D-manno-octulosonic acid (CMP-Kdo), and UDP-galactofuranose. Examples of monophosphonucleotide sugars which may be used in embodiments of the invention include cytidine monophosphate sialic acid (CMP-sialic acid), CMP-N-glycolylneuraminic acid (CMP-Neu5Gc), and CMP-N-Acetylneuraminic acid (CMP-Neu5Ac). Examples of lipid phosphosugars which may be used in embodiments of the invention include dolichol-P-glucose, dolichol-P-mannose, dolichol-P—P-(Glc$_3$-Man$_9$-GlcNAc$_2$), decaprenyl-P-arabinose, and undecaprenyl pyrophosphoryl N-acetylglucosamine. After transfer of the sugar, the donor becomes a leaving group, such as a nucleotide (eg. GDP, UDP, or CMP) or a phospholipid, having an exposed phosphate which may be removed by a phosphatase.

Acceptors which may be used in embodiments of the invention include any polysaccharide, oligosaccharide, protein, peptide, lipid, or glycoconjugate which can receive a monosaccharide or an oligosaccharide from a donor. In some embodiments, the acceptor may be water.

After release of the phosphate from the leaving group by the phosphatase, the free phosphate may be readily detected and/or measured by any means. In some embodiments, the free phosphate may be detected and/or measured using a colorimetric assay. Examples of colorimetric assays for measurement of free phosphate which may be used in embodiments of the invention include the Malachite Green Phosphate Detection Kit available from R & D Systems, (Minneapolis, Minn.), PiColorlock™ Assay reagent available from Innova Biosciences, Ltd. (Cambridge, U.K.), and Phosphate Colorimetric Assay Kit available from BioVision (Mountain View, Calif.). In other embodiments, the free phosphate may be detected and/or measured by fluorenscense detection. For example, free phosphate may be selectively detected by a fluorescent sensor as described in U.S. Pat. No. 7,521,250, the disclosure of which is hereby incorporated by reference. In another example, free phosphate may be detected using a recombinant *E. coli* phosphate-binding protein labeled with the fluorophore MDCC known as Phosphate Sensor and available from Invitrogen (Carlsbad, Calif.).

The Malachite Green Phosphate Detection Kit is one method that may be used to detect free phosphate and is based on the malachite green-molybdate binding reaction, and the kit itself, or the components or variations thereof, may be used in embodiments of the invention. The Malachite Green assay includes a first reagent, Malachite Green Reagent A, which includes ammonium molybdate and sulfuric acid, and a second reagent, Malachite Green Reagent B, which includes malachite green oxalate and polyvinyl alcohol. The Malachite Green assay further includes a phosphate standard, $KH_2PO_4$. The phosphate standard may be used to create a standard curve of absorbance at 620 nm for interpretation of sample assay results. The method includes incubating a sample with Malachite Green Reagent A for 10 minutes at room temperature, then adding Malachite Green Reagent B and incubating for 20 minutes at room temperature. The absorbance may then be read at 620 nm and compared to the phosphate standard curve to determine the amount of phosphate present in the sample. The Malachite Green Phosphate Detection kit itself, or components or variations thereof, may therefore be used to detect levels of free phosphate released from a leaving group by a phosphatase, or constituting a leaving group itself, according to embodiments of the invention. In such embodiments, known amounts of the donor, acceptor, glycosyltransferase, and optionally phosphatase are combined to produce a sample for testing. In some embodiments, the sample may further include an additional component, such as a potential glycosyltransferase inhibitor. The resulting sample may be combined with Malachite Green Reagent A and then Malachite Green Reagent B. The absorbance may then be read at 620 nm, and the reading may be correlated to a phosphate standard and a control including all reaction components except the glycosyltransferase enzyme, to determine the amount of free phosphate released by the phosphatase. This amount may be compared to the initial quantity of donor and/or glycosyltransferase present in the sample to determine the activity of the glycosyltransferase and/or the affect of any additional components upon the glycosyltransferase activity.

Embodiments of the invention include an assay or kit for measuring glycosyltransferase activity. The assay may be used for evaluation of the activity of a glycosyltransferase with a particular donor and/or acceptor. In some embodiments, the assay may be used for studying the glycosyltransferase to determine activity with various donors and acceptors and reaction kinetics. In still other embodiments, the assay may be used to evaluate the effectiveness of an agent at altering the activity of a glycosyltransferase, such as promoting, inhibiting or blocking the activity of the glycosyltransferase. For example, embodiments of the invention may be used to assess or test for the effectiveness of an agent, such as a potential antibiotic agent, at inhibiting or blocking the activity of a glycosyltransferase. In still other embodiments, the assay may be used for determining the dose response of glycosyltransferase to an agent.

In one embodiment, a glycosyltransferase assay kit includes a phosphatase and a free phosphate detector which may be provided in separate vials, for example. In some embodiments, the kit further includes one or more nucleotides. The nucleotides may be the same as the leaving groups which would be produced by the glycosyltransferase which would be used with the assay kit. In some embodiments, the kit further includes an assay buffer. In some embodiments, the kit includes a phosphate standard.

In one embodiment, a glycosyltransferase assay kit includes CD39L3 (ENTPD3) (such as recombinant human CD39L3 having a specific activity of greater than 70,000 pmol/min/µg, available from R & D Systems) as a phosphatase and Malachite Green Reagent A and Malachite Green Reagent B as a free phosphate detector. The kit may further include UDP, GDP, a phosphate standard (such as $KH_2PO_4$) and/or a standard assay buffer, and the UDP and/or GDP may be provided in the standard assay buffer. Additional assay kit components may include a donor sugar-nucleotide, an acceptor substrate, and/or a glycosyltransferase, each of which may alternatively be provided as part of an assay kit or may be separately provided by the kit user. For example, the assay kit may further include GDP-fucose as a fucose donor, N-acetyllactosamine as an acceptor substrate, and/or Fut5 (such as recombinant human Fut5, available from R & D Systems) as a glycosyltransferase, or these may be provided by the user for use with the assay kit. In another embodiment, a glycosyltransferase assay kit includes CD73 (such as recombinant human CD73, having a specific activity of greater than 15,000 pmol/min/µg, available from R & D systems) as a phosphatase and Malachite Green Reagent A and Malachite Green Reagent B as a free phosphate detector. The assay kit may further include CMP, a phosphate standard ($KH_2PO_4$), and/or a standard assay buffer, and the CMP may be provided in the standard assay buffer. Additional assay kit components may include a donor sugar-nucleotide, an acceptor substrate, and/or a glycosyltransferase, each of which may alternatively be provided as part of an assay kit or may be separately provided by the kit user. For example, the assay kit may further include CMP-NeuAc as a sialic acid donor, N-acetyllactosamine as an acceptor substrate, and/or ST6GAL1 (such as recombinant human ST6GAL1, available from R & D Systems) as a glycosyltransferase, or any of these may be provided by the user for use with the assay kit.

In some embodiments, the assay buffer provided with or used with the assay is compatible with the phosphatase. For example, the buffer may be phosphate free. In addition, any other reagents used in the assay may be phosphate free. In some embodiments, the standard assay buffer may include Tris, $MnCl_2$, $MgCl_2$, $CaCl_2$ and may have a pH of approximately 7.0. In some embodiments, the buffer and other reagents have low levels of divalent cations such as calcium, magnesium and manganese. In other embodiments, the phosphatase is not active in the assay buffer used with or provided with the assay. In such embodiments, the donor, acceptor, and glycosyltransferase may first be combined in a first buffer which is the glycosyltransferase assay buffer. A second buffer which is the phosphatase buffer may then be added to this to overpower the glycosyltransferase assay buffer. The phosphatase may be added with the phosphatase buffer or may be added separately, after addition of the phosphatase buffer. The phosphatase buffer may be stronger than the glycosyltransferase assay buffer, such that the conditions provided by the phosphatase buffer will overwhelm those provided by the glycosyltransferase assay buffer, with the resulting mixture being more similar to the phosphatase buffer and therefore preventing disruption of the phosphatase activity.

In order to correlate assay results to levels of free phosphate, and thereby to glycosyltransferase activity, standard curve such as a phosphate standard curve may be produced. In embodiments in which a Malachite Green assay is used to measure free phosphate, and in embodiments using other free phosphate detection methods as well, the phosphate standard curve may be made using serial dilutions, such as 2-fold serial dilutions, of a phosphate solution such as the phosphate standard, in the assay buffer. For example, the serial dilutions may be as in Table 1, below.

TABLE 1

| Well | Phosphate concentration (μm) | Phosphate input |
| --- | --- | --- |
| 1 | 50 | 5,000 |
| 2 | 25 | 2,500 |
| 3 | 12.5 | 1,250 |
| 4 | 6.25 | 625 |
| 5 | 3.13 | 313 |
| 6 | 1.56 | 156 |
| 7 | 0.78 | 78 |
| 8 | 0 | 0 |

When the Malachite Green assay is used, for example, the serial dilutions may be added to a clear 96-well plate and may be performed in triplicate. The Malachite Green Reagent A is first added to each well, followed by the Malachite Green Reagent B. After 20 minutes, the optical density is read at 620 nm (OD620) for each well using a microplate reader or spectrophotometer. The average reading for each dilution may be obtained. The phosphate input may be plotted against the results, or the average of the results for each dilution, to create a standard curve, such as by using linear regression or a computer generated four parameter logistic (4-PL) curve fit. A similar curve may be obtained using other free phosphate detection methods or other phosphate sources. The slope of the linear regression line may be used as the conversion factor to determine how much phosphate corresponds to each absorbance unit.

Embodiments of the invention further include methods of measuring glycosyltransferase activity. The glycosyltransferase to be assayed may be first isolated or produced or obtained from commercial sources. A sugar donor, an acceptor substrate and a glycosyltransferase enzyme may be combined in a buffer to produce a product. A phosphatase may then be added to the product. Alternatively, a phosphatase may be combined with the sugar donor, acceptor and glycosyltransferase in a coupling reaction to produce a product. Next, the amount of free phosphate may be measured and this amount may be used to calculate the activity of the glycosyltransferase enzyme. For example, the amount of free phosphate may be measured by measuring a signal, such as light absorbance (optical density, or O.D.) or fluorescence. In some embodiments, measuring the amount of free phosphate includes applying a colorimetric test and comparing the to a standard free phosphate absorbance curve.

In some embodiments, the method may be used to assay the glycosyltransferase with various donors and or acceptors. The method allows for such testing because of the high through put nature of the method disclosed herein. The glycosyltransferase may be combined with a first donor and a first acceptor and a phosphatase, such as in a well of a 96 well microplate, to produce a first reaction. Alternatively, the reactions may be carried out in any multiwell plate. In a second reaction, the glycosyltransferase may be combined with a second donor and a second acceptor and a phosphatase, where the second donor and second acceptor are each different from the first donor and acceptor. Alternatively, either one of the second donor or second acceptor may be the same as the first donor and first acceptor. Additional reactions may be performed using additional donors and acceptors. The free phosphate produced in each reaction may then be measured and the activity of the glycosyltransferase can be calculated for each donor and acceptor combination. In some embodiments, each reaction will be combined with Malachite Green reagent A and then Malachite Green reagent B. The absorbance will be read at 620 nm and the results will be used to determine the amount of free phosphate present in each sample. The activity of the glycosyltransferase with each donor and/or acceptor present in each reaction can thereby be compared. In some embodiments, the amount of phosphate source (e.g., phosphate standard, donor, or leaving group) used is calculated so that the final amount of phosphate present in the microwell will be between about 200 and 2,000 pmol. In other embodiments, the glycosyltransferase activity may be assayed in the presence of a test substance, such as a potential drug such as an antimicrobial agent, wherein the additional component is being tested for its effect upon the glycosyltransferase activity. For example, the test substance may increase, decrease or block the activity of the glycosyltransferase. In such embodiments, the glycosyltransferase is combined with a donor, acceptor, a test substance and a phosphatase. The free phosphate is then measured as described herein to determine the activity of the glycosyltransferase in the presence of the test substance. This activity may then be compared to the known activity of the glycosyltransferase under the same conditions. Alternatively, a separate reaction may be performed by combining the same glycosyltransferase, donor, acceptor and phosphatase under the same conditions, and measuring the free phosphate to determine the activity of the glycosyltransferase in the absence of the test substance. The two reactions may be performed simultaneously in separate wells of a microplate. The activity of the glycosyltransferase with and without the test substance may thereby be compared.

Additionally, multiple test substances may be simultaneously tested in the same manner to determine which, if any, have an effect upon the glycosyltransferase activity. In this way, the method of the invention may be used to quickly screen potential therapeutic agents for activity against a glycosyltransferase.

Substances which may be assayed as test substances include potential drugs or therapeutic agents such as antimicrobials, glycosyltransferase inhibitors, and nucleotide sugar mimetics, for example. Nucleotide sugar mimetics may be modified sugars, such as azido sugars, which may have a chemical handle that allows them to be recognized and detected by a detection reagent targeted to the handle after the nucleotide sugar mimetic is incorporated into a cell.

For each of the methods, one or more controls may be simultaneously (such as in separate wells) or separately performed, such as a phosphate standard. In some embodiments, a first control may include a phosphate standard curve which may be created by combining a source of free phosphate in a solution, wherein the solution is the same buffer as is used for the other assay, with a method of free phosphate detection, such as those provided in the Malachite Green detection kit. In some embodiments, a second control may include combining a leaving group, such as a nucleotide, with a phosphatase and then detecting the free phosphate. The nucleotide may be the same as the product which would be produced following removal of the sugar from the donor in the reaction with which the standard curve is being compared. Serial dilutions of the nucleotide may be performed, such as at least two or three dilutions or more, with each dilution being separately assayed with the phosphatase and phosphate detector. In this way, a curve may be produced for phosphate released from the nucleotide to test whether the phosphatase can quantitatively release phosphate from the nucleotide. The standard curve may be compared to assay results in which the donor is tested in the presence of the glycosyltransferase and acceptor, to determine the activity of the glycosyltransferase. As such, a first control may be performed to test the phosphate detection reagents and assay buffer with only free inorganic phosphate. A second control may be performed to test the phosphatase to see whether the phosphatase can release phosphate completely, such as across the expected nucleotide concentration range. The second control may produce a phosphatase curve which overlaps the free phosphate standard curve when both are plotted in a same graph. For each of the methods, the same reaction may be repeated, such as two or more times, such as three times, with each reaction being separately performed, such as simultaneously in separate wells of a microplate. The results of each reaction may then be averaged to reduce the effect of individual variation. The average results for each reaction may then be used for the evaluations and comparisons described herein.

Embodiments of the invention may be used for research regarding glycosyltransferase enzymes. They may be particularly useful for pharmaceutical development, such as for searching for glycosyltransferase targeted drugs.

EXPERIMENTAL

The GDP-Fucose, UDP-Glucose, CMP-NeuAc, CMP, UDP and GDP used in the following experiments were obtained from Sigma-Aldrich (St Louis, Mo.). The recombinant human Fut7, ST6Gal1, CD73, CD39L3, non-specific alkaline phosphatase TNAP, recombinant Clostridium Difficile toxin B (TcdB) containing the glycosyltransferase domain and Malachite Green Phosphate Detection Kit were obtained from R&D Systems (Minneapolis, Minn.). The 3'-Sialyl-N-acetyllactosamine was obtained from V-LABS, Inc (Convington, La.). Unless otherwise specified, each glycosyltransferase reaction was performed in 50 µL of a buffer of 25 mM Tris, 150 mM NaCl, 5 mM $MgCl_2$ and 5 mM $MnCl_2$, at pH 7.5 in a 96-well plate at room temperature for 20 minutes. To determine kinetic parameters of each glycosyltransferase, multiple reactions with varied amounts of either glycosyltransferase or substrates were preceded simultaneously in the presence of fixed amounts of all other components, including a phosphatase. A well containing all components except glycosyltransferase served as a blank control for each example. The reactions were stopped by adding 30 µL of Malachite Reagent A and 100 µL of water to each well. The color was developed by adding 30 µL of Malachite Reagent B to each well followed by gently tapping on the edge and incubation for 30 minutes. The plate was then read at 620 nm with a multi-well plate reader.

Example 1

UDP, GDP and CMP are common donors in glycosyltransferase reactions. Therefore, in order to select a phosphatase to couple to a particular glycosyltransferase reaction, up to 10 nmol of UDP, GDP and CMP were each separately treated with the phosphatases CD73, CD39L3, and TNAP in 50 µl of the glycosyltransferase assay buffer for 15 minutes in a 96-well plate in room temperature and then stopped with 30 µl of Malachite Reagent A and 100 µl water. The released phosphate in each well was revealed by addition of 30 µl of Malachite Reagent B. The color development in each well corresponded to the phosphate release. The results were then compared to a standard phosphate curve that had an approximate slope of 0.25 OD/nmol, as shown in FIG. 4. As shown in FIG. 4A, CD73 at 0.1 µg level could dephosphate CMP completely under the conditions. FIG. 4B shows that CD39L3 at 0.1 µg level could release one molar equivalent phosphate from UDP and GDP under the same conditions. In FIG. 4C, it can be seen that TNAP, at 0.1 µg level, could only quantitatively release phosphate up to 2 nmol of nucleotide input. However, when the TNAP was increased to 1 µg as shown in FIG. 4D, it resulted in almost complete phosphate removal for all nucleotide inputs. It should be noted that about two molar equivalents of phosphate were released from UDP and GDP, indicating that these diphosphonucleotides released both phosphates. One molar equivalent of phosphate was released from CMP.

The results of this experiment demonstrate that phosphatases and phosphate detectors can be used to measure glycosyltransferase activity as the quantity of phosphate released in a sample is equal to the nucleotide input when phosphatase is present at a sufficient level. For example, under these conditions, the 0.1 µg CD73 was sufficient to couple to up to 10 nmol of CMP released from sialyltransferase reactions. Likewise 0.1 µg CD39L3 was sufficient to couple to up to 10 nmol of UDP and GDP released from glucosyltransferase or fucosyltransferase reactions. 1 µg TNAP is sufficient to quantitatively release phosphate from 10 nmol of CMP, UDP or GDP under the specified conditions.

Example 2

Hydrolase Activity of TcdB Assayed with CD39L3

Figure 5:
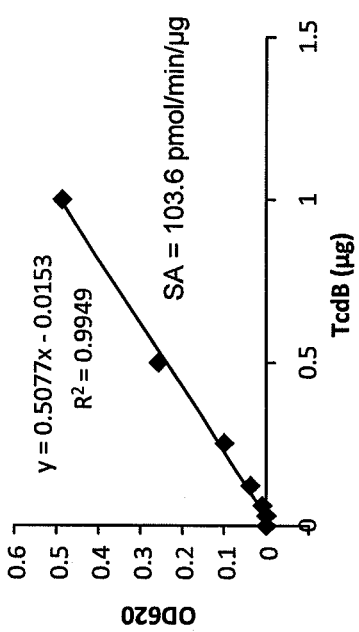
FIG. 5 is an enzyme dose curve for TcdB.

Toxin Clostridium difficile B (TcdB) is a UDP-glucose glycosyltransferase that exerts its cellular toxicity primarily through its ability to monoglucosylate, and thereby inactivate, Rho family small GTPases. TcdB has cation-dependent UDP-glucose hydrolase activity, which also can be considered as a glycosyltransferase activity, using water as acceptor molecule. Previous methods of assaying the enzyme employed radiolabled UDP-glucose and ion-exchange chromatography. In this example, the enzymatic activity of TcdB was measured in the presence of 0.1 µg CD39L3, 40 µM UDP-glucose, 10 mM $MnCl_2$, 5 mM $CaCl_2$ and 150 mM $K_2SO_4$ at pH 7.5 in a 96-well plate at room temperature. The results are shown in FIG. 5. A standard phosphate curve was produced as described above to calculate a conversion factor of 4081 pmol/OD. Using this conversion factor, the specific activity of the enzyme under the specified conditions was determined to be 103.6 pmol/min/µg.

Example 3

Transferase Activity of Fut7 on 3'-sialyl-N-acetyllactosamine Assayed with CD39L3

Figure 6:
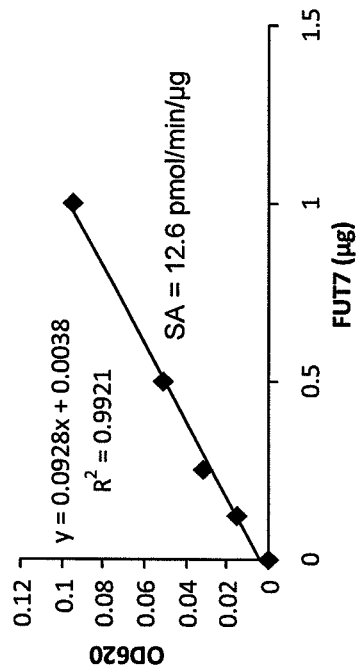
FIG. 6 is an enzyme dose curve for FUT7.

The only known function of fucosyltransferase 7 (Fut7) is the biosynthesis of sialy Lewis X epitope in leukocytes and high endothelial venule cells. Previous methods of assaying the enzyme used a radiolabed donor substrate and ion-exchange chromatography. In this example, varied amounts of Fut 7 were incubated with 0.1 µg CD39L3, 40 µM each of GDP-fucose and 40 µM 3'-sialyl-N-acetyllactosamine in a 96 well plate at 37° C. for 30 minutes. The reaction was then stopped and detected by malachite reagents. The results are shown in FIG. 6. A standard phosphate curve was produced as described above to calculate a conversion factor of 4081 pmol/OD. Using this conversion factor, the specific activity of the enzymes under the specified conditions was 12.6 pmol/min/µg.

Example 4

Sialyltransferase Activity of ST6Gal 1 Assayed with CD73

Figure 7:
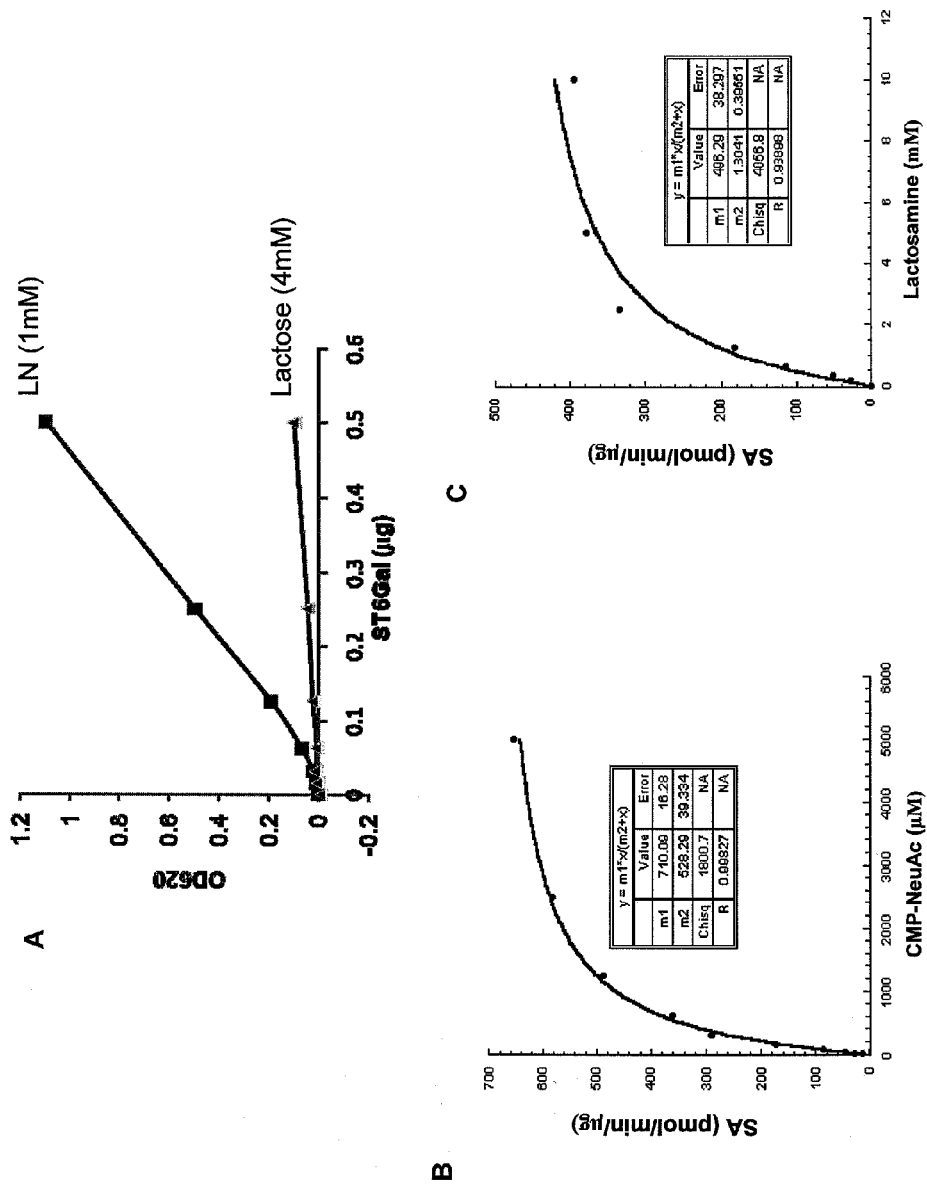
FIG. 7A is an enzyme dose curve for CMP-NeuAc using either lactosamine or lactose as an acceptor substrate.
FIG. 7B is a donor substrate curve for ST6Gall in lactosamine.
FIG. 7C is an acceptor curve for ST6Gall in CMP-NeuAc.

Sialic acid is negatively charged under normal pH conditions, making sialyltransferases more difficult to assay than other glycosyltransferases. Because both the donor and product are likely negatively charged, separating them by common ion exchange chromatography separation is challenging. In this experiment, ST6Gal 1, a sialyltransferase, was assayed using 0.1 µg CD73 in a 96-well plate. First, enzyme curves were obtained with either 1 mM lactosamine or 4 mM lactose as the acceptor in the presence of 1 mM CMP-NeuAc. The results are shown in FIG. 7, and the specific activities against lactosamine and lactose were determined to be 458 and 41 pmol/min/µg respectively, confirming that the enzyme strongly favors lactosamine structure. The apparent $K_m$ and $V_{max}$ were determined for one substrate while fixing the other by fitting the data to KaleidaGraph 4 program. When lactosamine was fixed at 1 mM, the $K_m$ for CMP-NeuAc was determined to be 0.53±0.04 mM and $V_{max}$ was 710±16 pmol/min/µg as shown in FIG. 7B. When CMP-NeuAc was fixed at 0.2 mM, the $K_m$ for the lactosamine was determined to be 1.8±0.4 mM and $V_{max}$ was determined to be 496±38 pmol/min/µg, as shown in FIG. 7C.

The invention claimed is:

1. A method of screening a test substance as an inhibitor of sialyltransferase enzyme activity comprising:

combining a sugar donor, an acceptor substrate, a sialyltransferase enzyme, a test substance, and a phosphatase in a buffer solution to produce a product, wherein the phosphatase is 5'-nucleotidase, wherein the phosphatase is not alkaline phosphatase, and wherein the product includes an amount of free phosphate;

measuring the amount of free phosphate present in the product;

using the measured amount of free phosphate to calculate the activity of the sialyltransferase enzyme in the presence of the test substance;

comparing the calculated activity of the sialyltransferase enzyme in the presence of the test substance to a known or measured activity of the sialyltransferase enzyme without the test substance; and designating the test substance as an inhibitor of the activity of the sialyltransferase enzyme when the calculated activity of the sialyltransferase enzyme in the presence of the test substance is lesser than the known or measured activity of the sialyltransferase enzyme without the test substance.

2. The method of claim 1, wherein measuring the amount of free phosphate in the product comprises applying a colorimetric assay to the product.

3. The method of claim 2 wherein applying the colorimetric assay to the product comprises:
   a) combining the product with a first reagent comprising ammonium molybdate and sulfuric acid;
   b) combining the product of step a with a second reagent comprising malachite green oxalate and polyvinyl alcohol; and
   c) measuring the light absorbance of the product of step b at 620 nm.

4. The method of claim 1 wherein the sugar donor comprises a sugar nucleotide.

5. The method of claim 4 wherein the sugar nucleotide is a sugar monophosphonucleotide.

* * * * *